United States Patent
Jaisinghani

[11] Patent Number: 5,425,265
[45] Date of Patent: Jun. 20, 1995

[54] APPARATUS AND METHOD FOR MEASURING THE CAPILLARY PRESSURE DISTRIBUTION OF POROUS MATERIALS

[76] Inventor: Rajan A. Jaisinghani, 4200 Northwich Rd., Midlothian, Va. 23112

[21] Appl. No.: 169,710

[22] Filed: Dec. 20, 1993

[51] Int. Cl.⁶ ............................................. G01N 15/08
[52] U.S. Cl. ........................................ 73/38; 73/865.5
[58] Field of Search ............................ 73/38, 865.5, 73

[56] References Cited

U.S. PATENT DOCUMENTS

| | | | |
|---|---|---|---|
| 3,524,341 | 8/1970 | Roy | 73/38 |
| 3,555,912 | 1/1971 | Lowell | 73/38 X |
| 3,683,674 | 8/1972 | Roy | 73/38 |
| 3,952,584 | 4/1976 | Lichstein | 73/73 |
| 4,625,544 | 12/1986 | Yuan et al. | 73/38 |
| 4,648,261 | 3/1987 | Thompson et al. | 73/38 |
| 4,660,412 | 4/1987 | Gupta | 73/38 |
| 4,718,270 | 1/1988 | Storr | 73/38 |
| 4,907,448 | 3/1990 | Givens | 73/38 X |
| 5,069,065 | 12/1991 | Sprunt et al. | 73/38 X |
| 5,245,859 | 9/1993 | Smith et al. | 73/38 |
| 5,297,420 | 3/1994 | Gilliland et al. | 73/38 |
| 5,361,627 | 11/1994 | Levesque | 73/73 |

*Primary Examiner*—Hezron E. Williams
*Assistant Examiner*—J. David Wiggins
*Attorney, Agent, or Firm*—Robert E. Bushnell

[57] ABSTRACT

A capillary pressure measuring device comprises a highly regulated low pressure control system with a vacuum producing subsystem, a sample holder, a vertical positioning mechanism and a weighing device used for measuring the advancing and receding capillary pressure distributions of porous materials using a wetting fluid. Advancing capillary pressure distribution of the porous materials are measured by the steps of applying a highly controlled pressure to a test sample which is in contact with the wetting fluid, so as to allow no or only limited absorption of the fluid in the sample; incrementally reducing the applied pressure and recording the stable or equilibrium fluid weight adsorbed at each increment of the reduced pressure; and calculating the advancing average sample cross section area based capillary pressure distribution and the pore size distribution using the weight absorbed versus applied pressure data. Receding capillary pressure distribution of the porous materials are measured by the steps of saturating the test sample with the wetting fluid; incrementally increasing the applied pressure and recording the release of the absorbed fluid from the test sample; and calculating the receding capillary pressure distribution and the receding average sample cross section area based pore size distribution based on the similar weight versus applied pressure data.

34 Claims, 9 Drawing Sheets

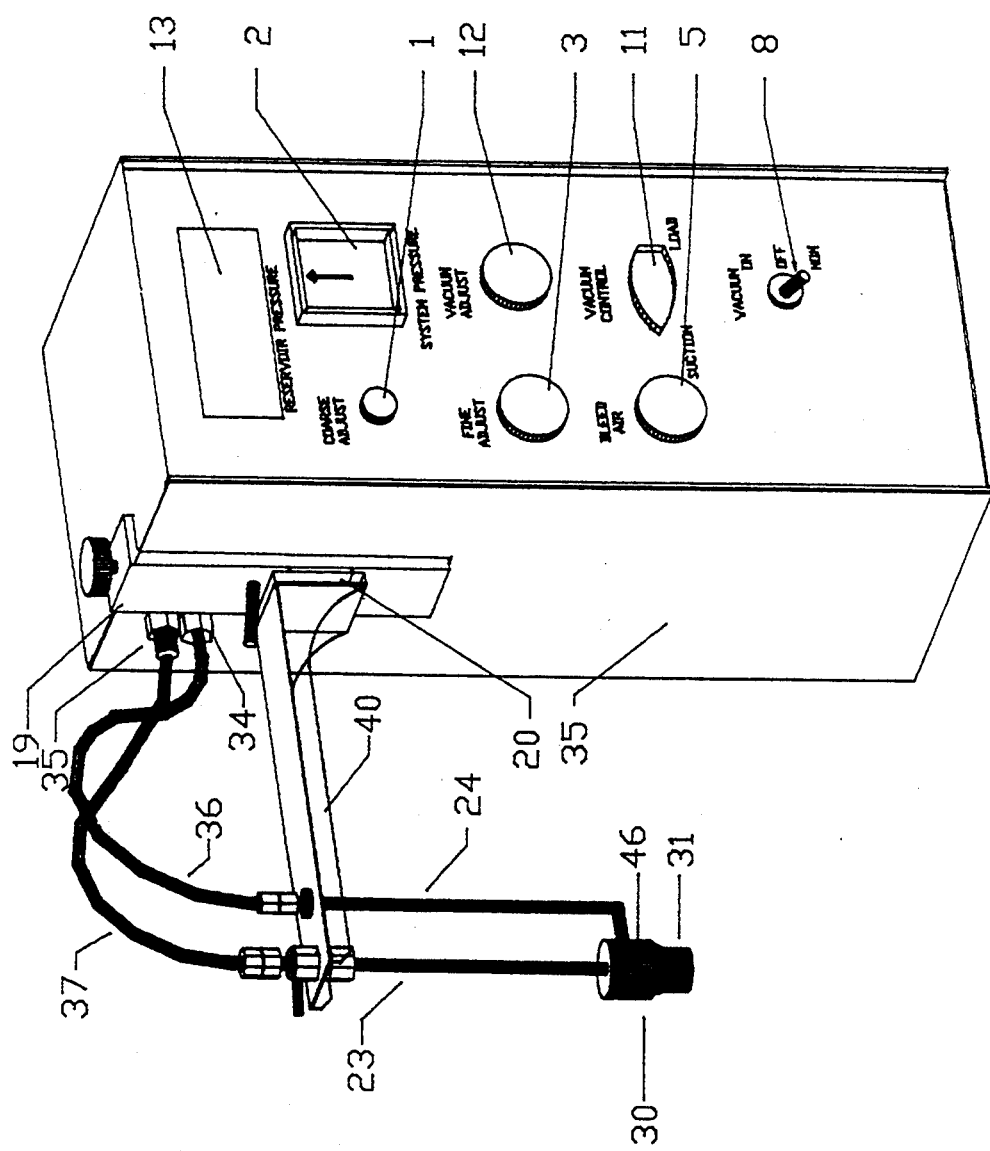

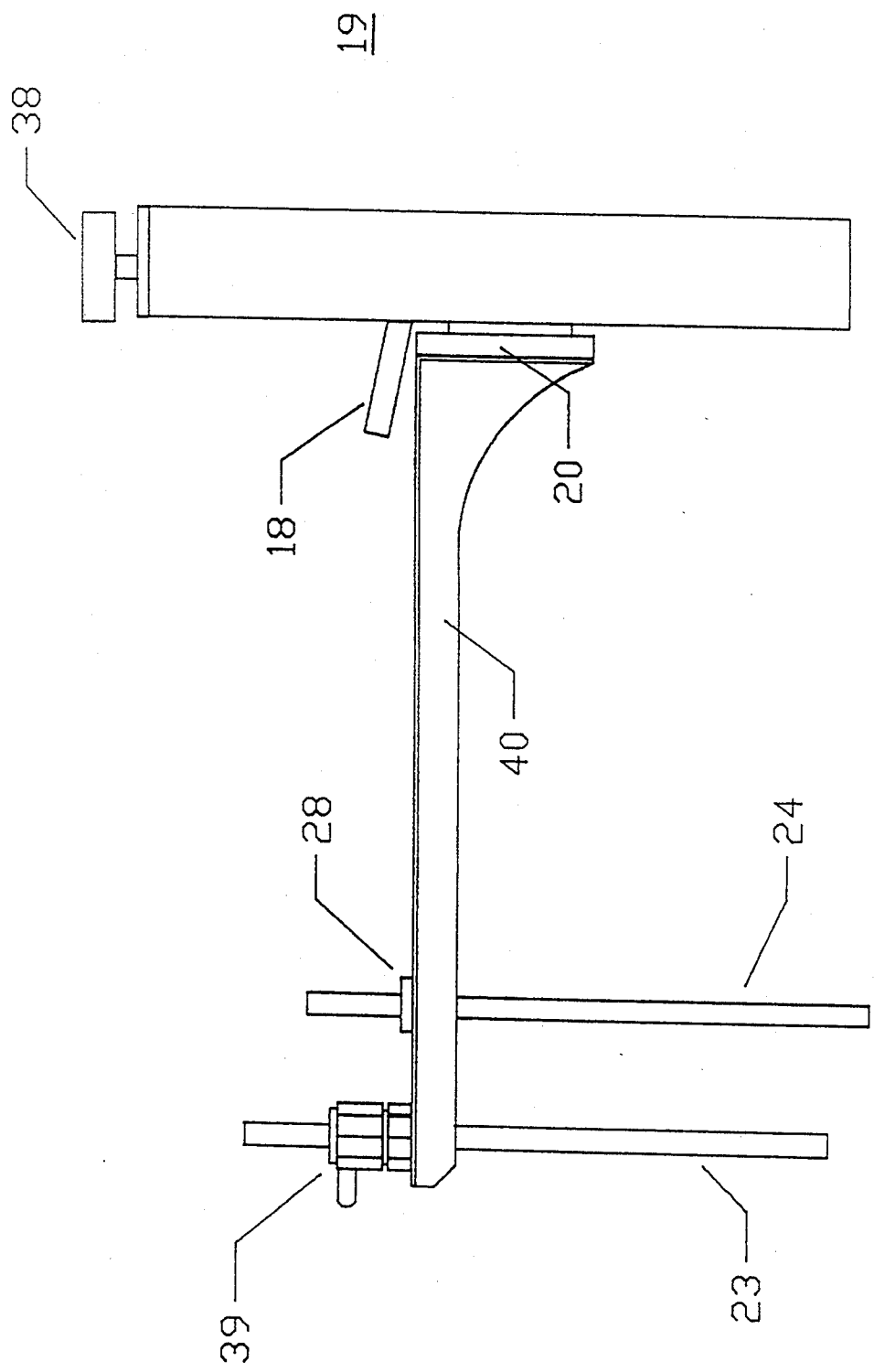

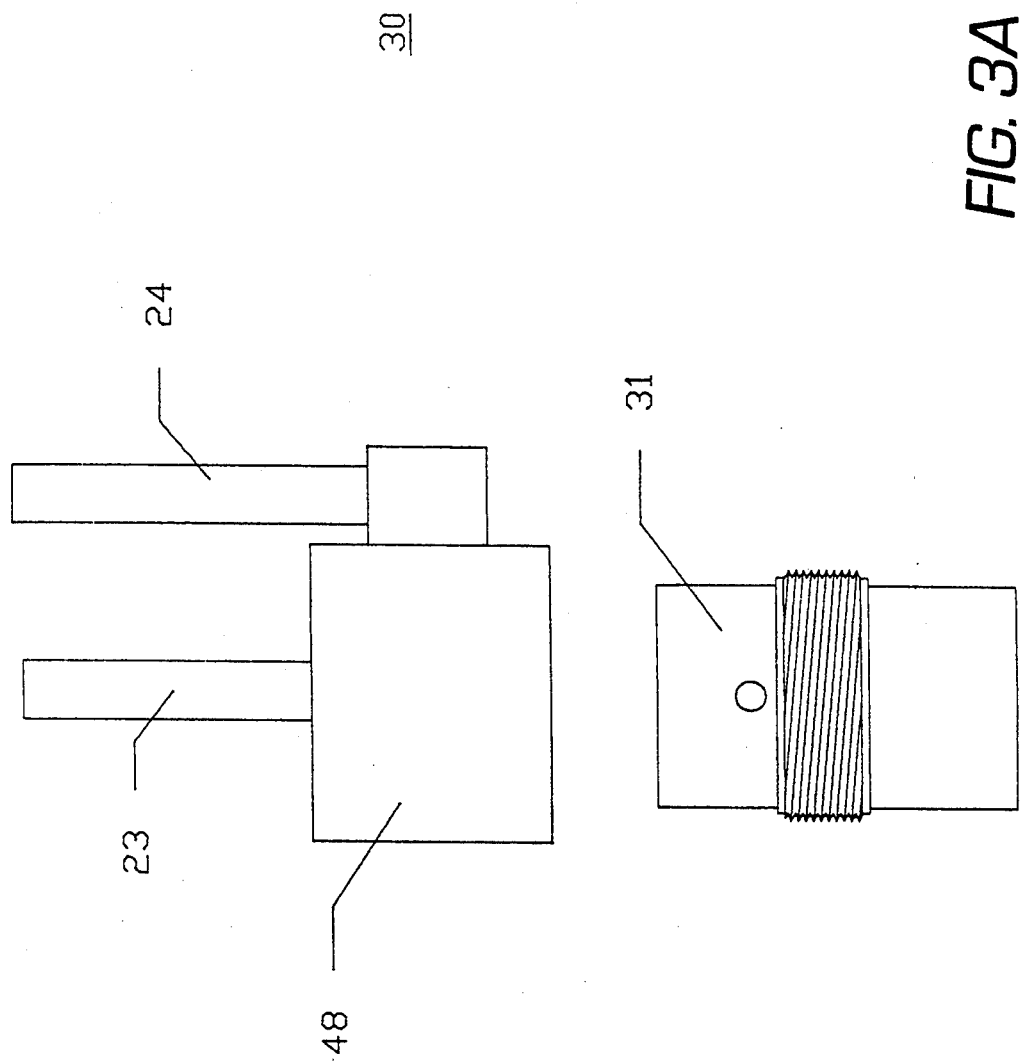

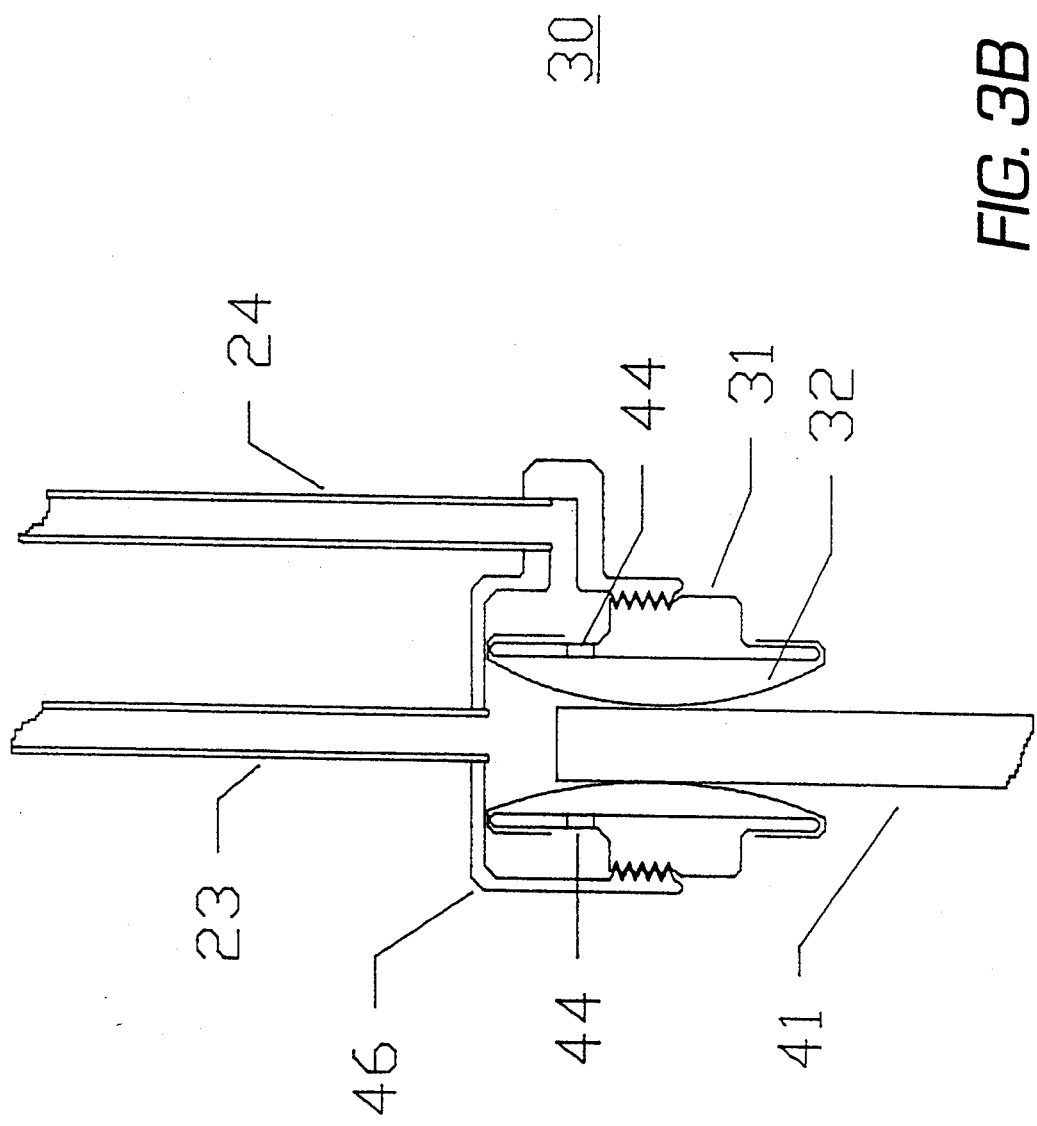

APPARATUS AND METHOD FOR MEASURING THE CAPILLARY PRESSURE DISTRIBUTION OF POROUS MATERIALS

FIELD OF THE INVENTION

This invention relates generally to a porosity-meter and more specifically to the method of measuring the advancing and receding capillary pressure distributions of porous materials using a wetting fluid.

BACKGROUND OF THE INVENTION

It is important to determine the capillary pressure of porous materials that are used in many applications such as writing instrument reservoirs, mono-clonal antibody based diagnostic test kits, filtration of immiscible fluids or gases with liquid dispersions and other applications that rely on porous materials for the transfer, absorption or release of liquids. In such applications, knowledge of the "pore" size distribution is not sufficient and often, is not very useful. The most common method for measuring the pore size distribution is mercury porosimetry (cf., Adamson, Wiley Interscience, N.Y. 1976), which relies on the measurement of intrusion of a non-wetting fluid, such as mercury Hg, into a test sample at increasing steps of applied pressure. There are many embellishments to the basic method. For example, *Determining Saturation And Permeability Using Mercury Capillary Pressure Curves* by Yuan et al. (U.S. Pat. No. 4,625,544) measures the response to a slow application of pressure against the mercury capillary pressure to learn more about the detail structure of the sample morphology. Still another variation is *Method For Measuring Wettability Of Porous Rock* by Sprunt et al. (U.S. Pat. No. 5,069,065) which displaces a first wetting fluid by a second non-wetting fluid that is immiscible with the first wetting fluid.

Yuan et al. '544 and Sprunt et al. '065 do not provide any information regarding the capillary pressure distribution of porous materials using a wetting fluid. The capillary pressure curves referred to in Yuan et al. '544 and Sprunt et al. '065 are simply mercury intrusion volume versus pressure curves. I have observed that these capillary pressure curves do not directly provide any information regarding the fractional area or volume based capillary pressure distribution of the porous material, as contemplated by the present invention. Prior methods calculate the pore size based on an assumption that the sample has a plurality of cylindrical and unconnected pores. The pore size distribution can be determined from the mercury Hg intrusion pressure-volume data as shown (cf. Adamson, Wiley Interscience, N.Y. 1976) in the following expression:

$$D(r) = (P/r)dV/dP, \quad (1)$$

where $D(r)$ is the pore radius based distribution function, $P$ is the applied pressure, $V$ is the volume of the mercury Hg injected and $r$ is the "pore" radius. It has been my observation that such assumptions are not generally valid, because the cross sections of the pores are varied, with expansions and contractions, and the pores themselves are often interconnected. Furthermore, as the porosity, defined as the void fraction, increases above approximately 0.7, the concept of "pores" breaks down and the applicability of the above equation (1) is doubtful.

In wetted fluid applications, the knowledge of the advancing and receding capillary pressure distribution with respect to the sample average cross section area or volume of the sample is required. This information is necessary for the design and development of liquid absorbency and release products. Advancing (of the liquid interface) and receding pressure curves exhibit hysteresis due to: a) non-uniformity of "pore" cross sections, b) existence of ink wells or dead ends, and c) differences in advancing and receding contact angle. Knowledge of either or both advancing and receding wetted fluid-sample capillary pressure distributions is important in the above applications depending on whether the porous sample is used for absorption (e.g., diagnostic test kits) or for absorption and liquid release (e.g., pen reservoirs). Mercury Hg porosimetry methods differ from the present invention in that only the pore size distribution is determined, using a non-wetting fluid, and that pressure must be applied in order for the non-wetting fluid to penetrate the porous sample, noting that in the above-mentioned wetted fluid applications of porous materials, the wetting fluid penetrate the sample without application of pressure.

There are other methods for measuring pore size distribution of porous samples that do not rely on Hg porosimetry. For example, *Pore Determination Of A Porous Member* by Roy (U.S. Pat. No. 3,524,341) determines the pore size distribution based on the change of conductivity of a previously saturated (with KCl) porous sample with respect to the displacement of the KCl by a pressurized gas. This results in the calculation of pore size distribution based on the receding flow of the KCl. Roy '341 does not present any method for calculating the sample cross-section area or volume based advancing or receding pore size distribution as determined by the present invention. Additionally, *Measurement Of Pore Size And Porosity* by Roy (U.S. Pat. No. 3,683,674) discloses a method that uses centrifugal force to release the saturated wetting fluid from the saturated porous sample. Once again, this method determines only the pore size distribution based on receding data. Roy '674 does not disclose a method for measuring the advancing interface based "pore" size, or any sample cross-section area, or volume based capillary pressure distribution. Both the Roy's methods in *Pore Determination Of A Porous Member* '341 and *Measurement Of Pore Size And Porosity* '674 utilize the receding displacement volume data for a wetting fluid, and make all the assumptions related to cylindrical pores in order to determine the pore size distribution. Furthermore, they do not determine the capillary pressure distribution of the porous sample.

Lowell, *Incremental Method For Surface Area And Pore Size Determination* (U.S. Pat. No. 3,555,912), proposes a method for measuring the pore size distribution based on gas absorption of a porous sample, that has been previously degassed. Storr, *Porosimeter And Methods Of Assessing Porosity* (U.S. Pat. No. 4,718,270), on the other hand, proposes an improvement to a method for determining pore size distribution based on gas flow rate versus pressure of gas that displaces a wetting fluid from a porous sample. I have observed that neither Storr '270 nor Lowell '912 proposes any method for calculating the sample average cross-section area or average volume based capillary pressure distribution. It is important to note that pore size measurements obtained by different physical principals give different results (cf. Adamson 1976). Hence, it is important to use methods that incorporate the same phenomena as the application or use of the porous materials. For example, wetted fluid absorption based measurements are more relevant when the porous material is used as an adsorbent, while mercury Hg displacement methods are more relevant to the displacement of non-wetting materials from a porous sample. The pore size distributions obtained by these different methods are also different. Hence, these methods are not suitable for porous materials used for absorbency and liquid release applications. Moreover, I have also observed that these methods do not measure the advancing and receding capillary pressure distributions of the porous materials; they can only calculate the "pore" size distribution of the porous materials. It is in my opinion that is fundamentally important to note that the prior art methods as disclosed by Yuan, et al. '544, Sprunt, et al. '065, Lowell '912, Storr '270 and Roy '341 and '674 as well as others do not provide for a method of determining the area or volume based advancing and receding capillary pressure distribution of porous materials.

SUMMARY OF THE INVENTION

It is therefore an object of the present invention to provide an improved method and apparatus for determining the sample average cross-section area or volume based advancing and receding capillary pressure distributions of porous materials.

It is another object to provide methods and apparatus for determining sample average cross-section area or volume based advancing and receding capillary pressure distributions of porous materials that are used with a wetting liquid for the purpose of fluid absorption, transport and release.

It is yet another object to provide a method for measuring the sample average cross-section area or volume based advancing capillary pressure distribution of porous materials.

It is still another object to provide a method for measuring the receding capillary pressure distribution of porous materials.

It is a further object to provide a method for measuring the sample cross-section area or volume based advancing and receding capillary pressure distribution of porous materials, and the pore size distribution based upon the advancing and receding capillary pressure distribution.

It is a still further object to provide a method and apparatus transforming the basic volume or weight versus applied pressure data into sample cross sectional area of volume based capillary pressure distribution functions of test samples, using a wetted fluid.

These and other objects may be achieved according to the principles of the present invention, with the advancing and receding capillary pressure distribution of porous materials using a wetting fluid, as well as the pore size distribution being measured by a novel capillary pressure measuring device which comprises a highly regulated low pressure control system with a vacuum producing subsystem, for applying a pressure and producing a vacuum; a sample holder for holding a porous sample; a vertical positioning mechanism for adjusting the porous sample in a vertical direction; and a weighing device for weighing the wetted liquid as it is absorbed or released by the porous sample over a number of intervals of the increased or decreased pressure. Advancing capillary pressure distribution of a porous sample is measured by the steps of applying highly controlled pressure to the porous sample such that there is little or no absorption, when the sample is lowered so as to just touch the wetted fluid surface; incrementally reducing the applied pressure and recording the equilibrium fluid weight absorbed into the porous sample at each increment of the reduced pressure; and calculating the advancing capillary pressure distribution and the pore size distribution based on the weight absorbed versus applied pressure data. Receding capillary pressure distribution of the porous materials are measured by the steps of saturating the porous sample with the wetting fluid; lowering the sample until it just touches the wetted fluid surface; incrementally increasing the applied pressure and recording the equilibrium release of the absorbed fluid from the porous sample at each increment of the increased pressure; and calculating the receding capillary pressure distribution and the receding pore size distribution based on the similar weight (of fluid in sample) versus applied pressure data.

Also in accordance with the present invention, the advancing capillary pressure distribution is calculated based upon the following equation:

$$f(P_a) = -g\,(dW/dP_a)P_a/(A_cE)_e \qquad (2)$$

where $f(P_a)$ is the advancing capillary pressure distribution function, W is the weight absorbed by the porous sample after adjusting for evaporation at particular applied pressure $(dW/dP_a)_{P_a}$ is the slope of the W versus $P_a$ curve at any particular applied pressure, Ac is the sample cross sectional area, E is the fractional porosity (void fractional), $P_a$ is the advancing capillary pressure and is equal to the applied pressure, $(A_cE)_e$ is the effective cross sectional void area of the porous sample, and g is gravity. Similarly, the receding capillary pressure distribution is calculated based upon the following equation:

$$f(P_r) = 1 + [g(dW/dP_r)P_{app}/(A_cE)_e] \qquad (3)$$

where $f(P_r)$ is the receding capillary pressure distribution function, W is the weight of the fluid in the porous sample at an applied pressure $P_{app}$, $P_r$ is the receding capillary pressure, $(A_cE)_e$ is the effective cross sectional void area of the porous sample, and g is gravity. $P_r$ depends on $P_{app}$ and is given by the following equation:

$$P_r = P_{app} + W_{max}g/(A_cE)_e \qquad (4)$$

where $W_{max}$ is the initial saturation weight of the fluid in the sample, prior to application of any pressure. The pore size distribution is calculated based upon one of the advancing capillary pressure distribution and the receding capillary pressure distribution, the contact angle of the porous sample in contact with the wetting fluid, and the surface tension of the wetting fluid.

BRIEF DESCRIPTION OF THE DRAWINGS

The above objects and other advantages of the present invention will become more apparent by describing the preferred embodiment of the present invention with reference to the accompanying drawings in which:

FIG. 1B illustrates an external embodiment of the apparatus and the control panel which enables access of all pressure indicators and control valves.

FIG. 2A illustrates a sample positioning mechanism with pressure and vacuum connecting tubes that attach to the sample holder.

FIG. 3A is an external view of the components of the sample holder.

FIG. 3B is a vertical cross sectional view of the sample holder illustrating the sample holding mechanism.

DESCRIPTION OF THE PREFERRED EMBODIMENT

Figure 1A:
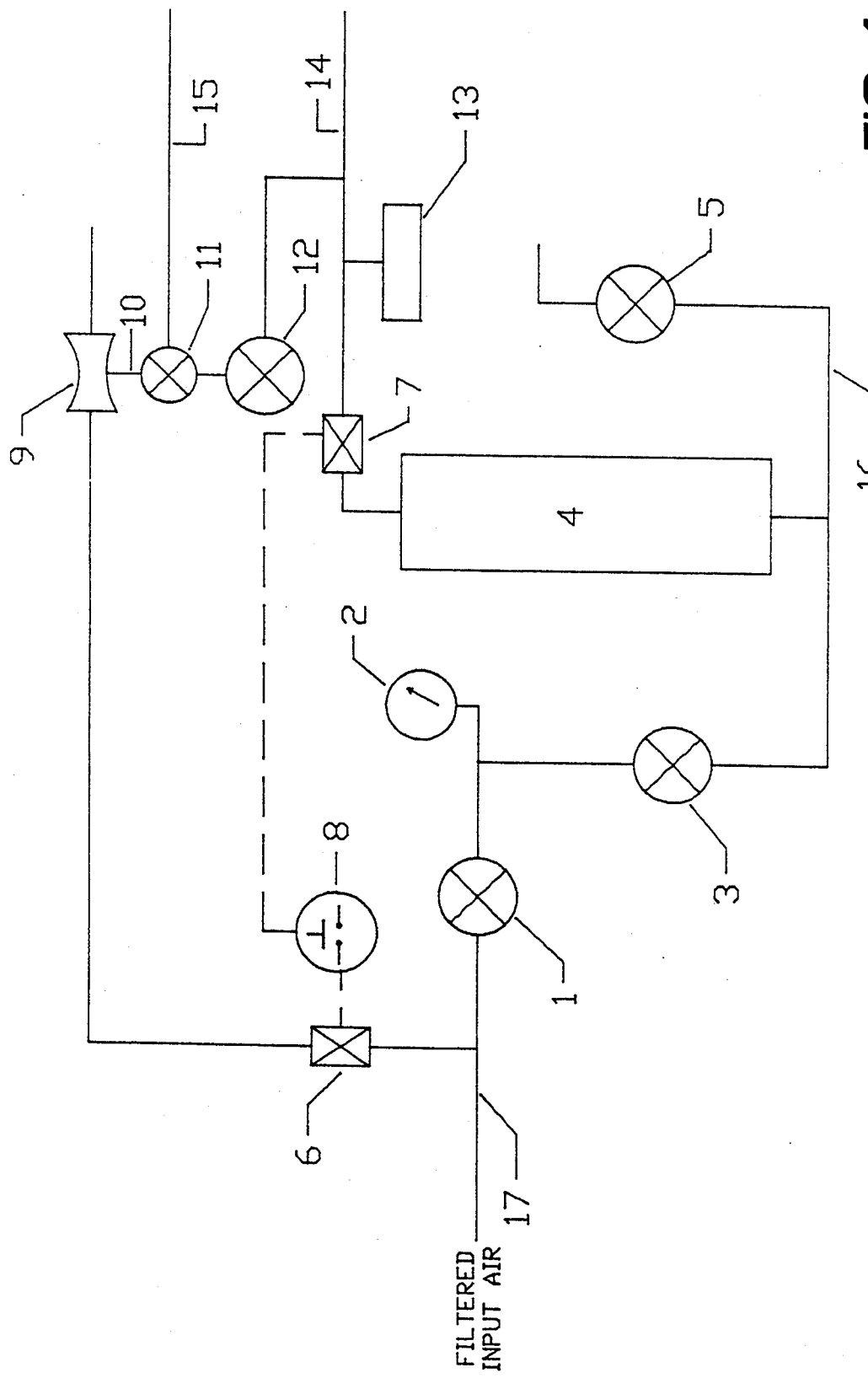
FIG. 1A is the flow schematic of the pressure control and vacuum producing subsystem of an apparatus for measuring both the advancing and receding capillary pressure distribution of porous materials.
Figure 2B:
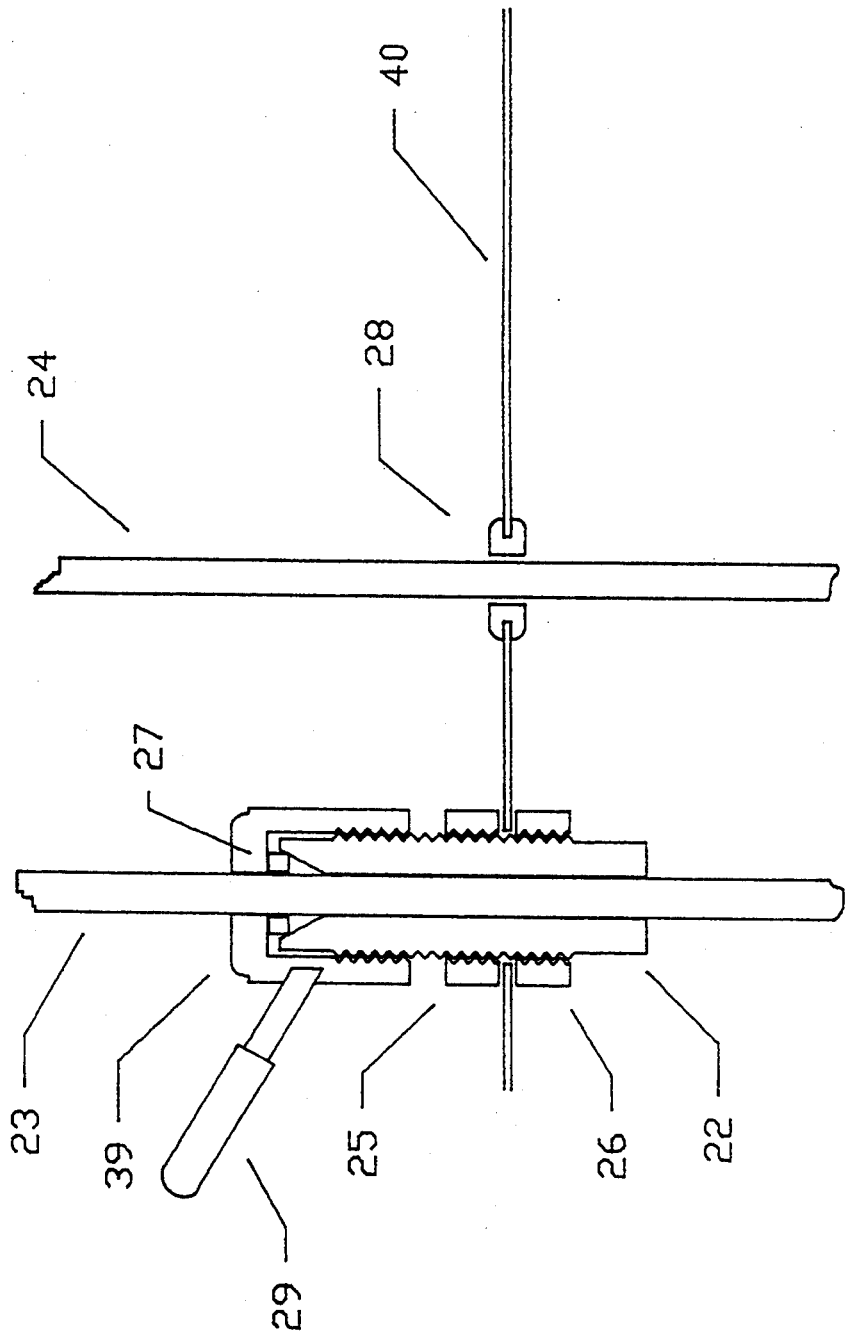
FIG. 2B illustrates a coarse positioning mechanism for the coarse vertical positioning of the pressure lines that attach to the sample holder and hence the coarse positioning of the sample holder.
Figure 4:
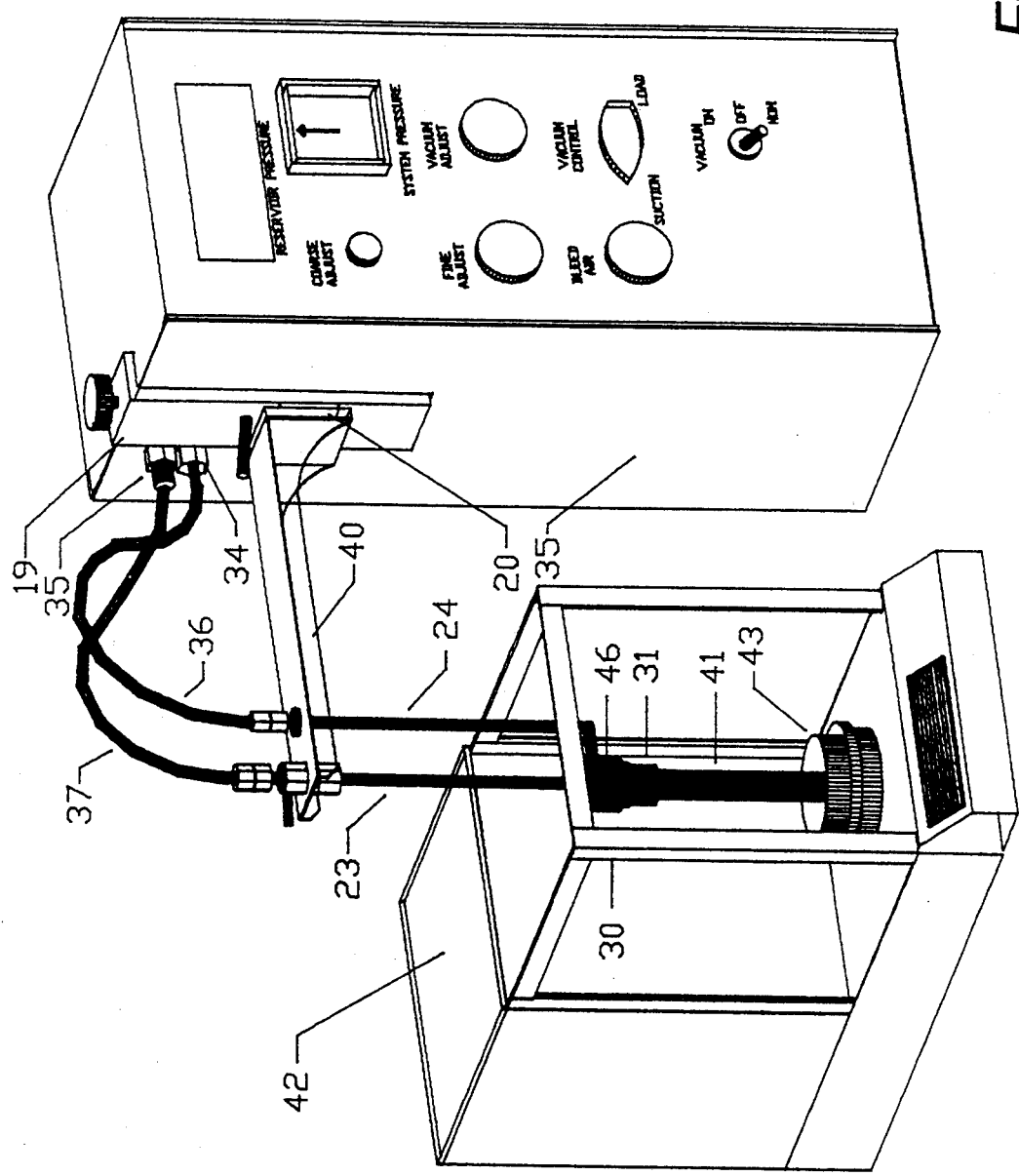
FIG. 4 is the overall view of the entire apparatus illustrating its use with a weighing balance.

Turning now to the drawings, in accordance with the present invention, the advancing and receding capillary pressure distributions of porous materials are measured by a novel capillary pressure measuring device which comprises a highly regulated low pressure control system with a vacuum producing subsystem as is shown in FIGS. 1A–1B, for applying a pressure and producing a vacuum to a porous sample in contact with a wetting fluid so as to enable either the porous sample to fully absorb the wetting fluid, or limit the absorption of the wetting fluid into the porous sample or release fluid from the sample; a sample holder as shown in FIGS. 3A–3B, for holding a porous sample; a vertical positioning mechanism as shown in FIGS. 2A–2B, for adjusting and positioning the porous sample within a weighing device as shown in FIG. 4 in order to measure the weight of fluid absorbed from or released into the wetted fluid container, over a number of intervals corresponding to the increased or decreased pressure at each interval.

Figure 5:
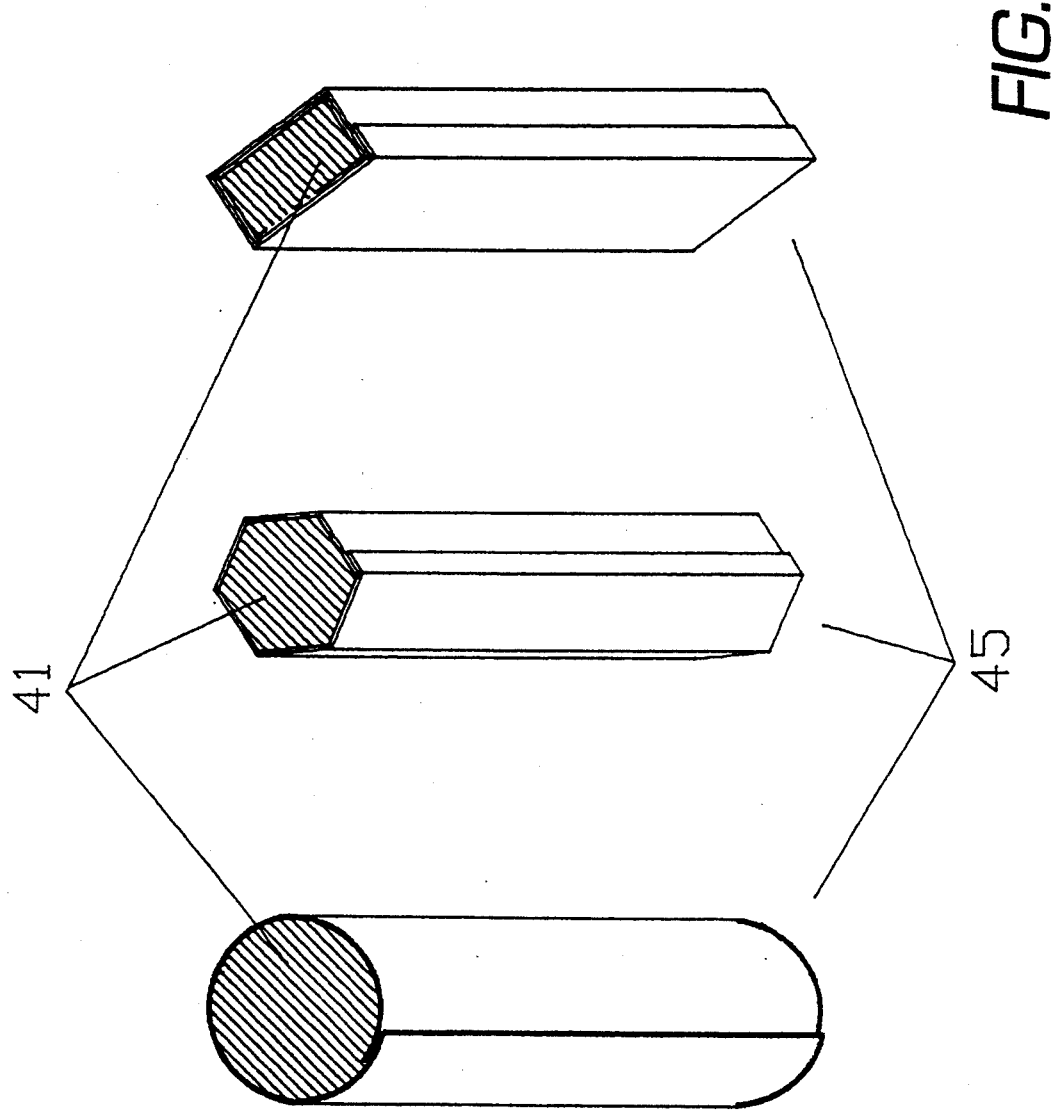
FIG. 5 illustrates some of the possible porous test sample shapes.

The novel capillary pressure measurement device (hereinafter "porosity-meter") as shown in FIGS. 1A–4, is compact and may have only four subsystems. The first subsystem consists of a highly regulated low air or gas pressure control and vacuum system as shown in FIGS. 1A–1B. The second subsystem consists of two vertical positioning mechanisms as shown in FIGS. 2A–2B. The third subsystem is a sample holding device as shown in FIGS. 3A–3C. The fourth subsystem is a weighing instrument (such as an analytical balance) or an accurate volume measuring device. The pressure control and vacuum subsystem, the positioning mechanism and the sample holder are incorporated into an instrument box 35. The instrument box 35 with the weighing balance 42 are shown in FIG. 4. Typical forms and shapes of the porous test samples are shown in FIG. 5. Preferably, the porous test sample should have a high length-to-width or diameter ratio and should have uniform cross section with respect to the sample length. Generally however, many porous test samples used are in a cylindrical form having a large length-to-width or diameter ratio, although non cylindrical forms such as multiple-sided forms, having uniform cross section with respect to the length, can also be used as shown in FIG. 5. Ordinarily, many porous materials, especially those of fibrous materials, are typically enclosed within a plastic film wrap. In case where the porous test sample is not wrapped in a plastic film, it must be wrapped in the plastic film and sealed along the longitudinal axis, without compressing the sample, so that only the top and bottom ends of the porous test sample are exposed as shown in FIG. 5. So long as the porous sample is wrapped in the plastic film, the porosity-meter should make the accurate determination of both the advancing and receding capillary pressure distributions of the porous test sample in a compact and easy to use approach, irrespective of whether it has different lengths and shapes.

The test porous sample is first installed in the sample holding device and positioned over the accurate weighing instrument or volume measuring device as shown in FIG. 4. The sample holding device having the test sample installed can then be lowered by the vertical positioning mechanism until it just touches the test fluid contained in a wide dish or container placed on the accurate weighing instrument or volume measuring device. Each of the above subsystems is first described in detail below.

Precise pressure control and vacuum generation

Referring to FIG. 1A–1B, FIG. 1A is a schematic flow diagram of the apparatus for controlling and regulating the low air or gas pressure, and producing a vacuum (negative pressure). This apparatus includes a primary or coarse low flow air pressure regulator 1, an air accumulator 4, and a bypass loop 16. Initial air pressure regulation is achieved by applying the supplied air which has been compressed and then filtered (typically by a 0.5 micrometer filter) to the inlet air pressure connector 17. The output of the primary pressure regulator 1 is set to approximately 1 to 4 psi as measured by a pressure gauge 2. Fine pressure control is obtained by varying the restriction of a metering valve 3 and by maintaining a minimum air flow through the bypass loop 16, which is controlled by a bypass metering valve 5 and a metering valve 3. A small amount of leakage of air flow is maintained through the bypass loop 16 by the metering valve 5, since it is well known that in order for air regulators to work accurately and efficiently, some air flow within the design range of the regulator must be maintained. The metering valve 3 is used to sufficiently restrict the air flow and thus reducing pressure in the air accumulator 4. The pressure in the air accumulator 4 is maintained at the required pressure by varying the restriction of the bypass metering valve 5. Note that typically there is little or no flow through the sample holder. Air accumulator 4 is a chamber with a large volume compared to the total volume of all the lines in the low pressure regulation system. The air accumulator 4 is used as a capacitor to dampen minor pressure fluctuations, and thereby outputting a constant pressure as measured by a pressure transducer 13. The pressure transducer 13 (typically a strain gauge or a variable reluctance transducer-with a typical range of 0 to 20 inches water column) measures the positive or negative pressure (vacuum) present in the regulated air pressure or vacuum output tube 14, which is connected to the sample holder.

This subsystem can also be used to produce a vacuum to the sample holder 30, although a separate vacuum source may be used instead of this subsystem. A vacuum is produced when the filtered input air is redirected through a venturi 9. The input air is redirected into the venturi when electrical power is applied by means of closing vacuum switch 8 so as to open a first solenoid valve 6 and to simultaneously close a second solenoid valve 7. The first solenoid valve 6 is a normally closed electrically operated valve. The second solenoid valve 7 is a normally open electrically operated valve. When electrical contact is made by the vacuum switch 8, the first solenoid valve 6 is opened and the second solenoid valve 7 is closed simultaneously, allowing the filtered compressed air to flow through the venturi 9, thereby producing a vacuum (negative pressure) in tube 10, which is attached to the throat of the venturi 9, near it's vena contracta. The second solenoid valve 7 is closed to prevent vacuum or negative pressure into the accumulator 4. 3-way valve 11 is used to direct the vacuum to either a maximum vacuum output tube 15 or to a metering valve 12. The metering valve 12 is used to control or regulate the vacuum to a vacuum output tube 14 which is connected to a sample holder tube 23 as shown in FIG. 3A. Vacuum is directed to the vacuum output tube 14 when controlled low vacuum is needed in order to draw the fluid up from the container into the test sample. The maximum vacuum output tube 15 is connected to the vacuum tube 24 (See FIG. 3A) of the sample holder. When the test sample needs to be inserted or removed from the sample holder, the vacuum is directed to the maximum vacuum output tube 15 by the 3-way valve 11 so as to provide maximum vacuum for quick opening of the latex insert 32 within the sample holder 30 (as described later in FIG. 3B).

FIG. 1B is a three dimensional view illustrating how the various control and indicating components are arranged in an instrument box or a housing 35. The air pressure gauges 2 and 13 are mounted as high as possible on the front of the housing 35 for easy viewing. The valve handles of the valves 1, 3, 5, 11, 12 are mounted lower so the visibility of the air pressure gauges 2 and 13 is not obstructed when the valves are adjusted. The vacuum switch 8 is mounted near the base of the housing 35 in order to minimize shifting or vibration when pressure is applied to the vacuum control switch 8. Tubing connectors 33 and 34 connect or disconnect flexible tubes 36 and 37 to internal tubes 14 and 15. This enables removal of the flexible tubes 3G and 3F for cleaning, without requiring the opening of the housing 35. A vertical positioning mechanism 19 is connected to the side of the housing 35 and a horizontal positioning bracket 40 is mounted horizontally to the vertical positioning mechanism 19. Coarse positioning tubes 23 and 24 are mounted on the horizontal positioning bracket 40; and the sample holder 30 is attached to the coarse positioning tubes 23 and 24. The filtered compressed supply air is connected to an inlet tube 17 (not shown) at the rear of the housing 35.

Vertical Positioning

Referring to FIGS. 2A–2B, FIG. 2A illustrates the vertical positioning mechanisms used to precisely raise or lower the test sample holder 30 and hence the test sample 41. To provide the necessary travel distance so as to reach inside the weighing measuring device, two separate methods of raising and lowering the test sample holder are employed. The first vertical positioning mechanism consists of a linear slide stage mechanism 19, typically a precision screw or a rack and a pinion type mechanism. A slip clutch 18 engages or disengages an adjusting screw 21 from a mounting plate 20, providing for quick, coarse, positioning of the horizontal positioning bracket 40 which is mounted on the plate 20. Precision vertical positioning of the horizontal positioning bracket 40 is accomplished by turning a knob 38, which is affixed to the adjusting screw 21. The second vertical positioning mechanism provides for further coarse large distance adjustment. This is shown in FIGS. 2A–2B. This second vertical positioning mechanism consists of the pressure and vacuum tubes 23 and 24, a guide tube 22, a grommet 28, a retaining nut 39 with a lever 29 and a rubber washer 27. Vertical positioning is accomplished by sliding the coarse tube 23 positioning inside the guide tube 22 and tightening the retaining nut 39 in order to secure the pressure tube 23 in a fixed place. The guide tube 22 is a threaded smooth bore tube having a bore diameter slightly larger than pressure tube 23, and is secured to the horizontal positioning bracket 40 by nuts 25 and 26. The inlet of the guide tube 22 is tapered so that when the retaining nut 39 is tightened, and the rubber washer 27 is compressed against the pressure tube 23 in order to prevent the pressure tube 23 from sliding up and down. The handle 29 is affixed to the retaining nut 39 in order to tighten or loosen the retaining nut 39 without requiting a wrench. The grommet 28 is used so as to provide a smooth sliding surface for the vertical movement of the vacuum tube 24 and to prevent twisting of the sample holder 30 during the replacement of the adaptor 31 (See FIG. 3A). This ensures that the sample holder 30 is properly aligned in the vertical direction.

Referring to FIG. 1B to FIG. 4, the linear slide stage mechanism 19 is attached to the side of the housing 35, at a distance high enough so that when the mounting plate 20 is at its lowest vertical position, there is sufficient distance for the horizontal positioning bracket 40 to clear the top of the weighing balance 42. The regulated pressure tube 23 and the vacuum tube 24 are long enough so that with the mounting plate 20 in its lowest position, and the adaptor 31 installed in the sample holder 30, the adaptor 31 is able to touch the balance weight platform. This allows for a sufficient travel distance in the vertical positioning in order to enable the testing of porous samples having a variety of lengths.

Tubes 36 and 37 are flexible so as to enable vertical movements while they are still tightly connected to the pressure controlling and vacuum producing device. The flexible tube 37 connects the connector 33 (attached to the pressure tube 14 as shown in FIG. 1A) to the pressure tube 23. The flexible tube 36 connects the connector 34 (attached to the maximum vacuum output tube 15 as shown in FIG. 1A) to the vacuum tube 24.

The horizontal positioning, for placement over the weighing device, is achieved by attaching the horizontal positioning bracket 40 to the mounting plate 20 of the linear slide stage mechanism 19.

Sample Holder

Referring to FIGS. 3A–3B, the holder assembly provides a method of easily attaching and replacing the test sample 41. This is done in a manner such that there is an insignificant amount of air leakage between the latex insert and the test sample 41, and at the same time ensuring that the test sample 41 is not significantly compressed or constricted. The holder assembly holds the test sample in place during the capillary pressure distribution test. The appropriate gripping pressure for various size test samples is controlled using a set of adapters 31 of different diameters with latex inserts 32 of corresponding sizes. The test sample 41 is installed and removed by applying a vacuum through the vacuum tube 24 via the maximum vacuum tube 15 (by turning on the switch 8 as shown in FIG. 1A). This vacuum causes the latex insert 32 to expand, thus enabling the insertion or release of the test sample. Once the top of the sample is positioned within the expanded latex insert 32, the vacuum is released by opening switch 8, causing the latex insert 32 to gently constrict around the top of the sample 41, thus holding it in place. FIG. 3A is a three dimensional view of the sample holder 30 and illustrates the holder assembly. The holder base 46 has female threads for screwing in the adaptor 31. The adaptor 31 is interchangeable by simply unscrewing it from the holder base 46 and replacing it with a different size adaptor 31 into the holder base 46. The different adapters have a common outer diameter but have different internal diameters so that different size latex inserts 32 can be used. The latex insert 32 is roughly in a cylindrical form having two open ends. FIG. 3B is a detailed cut away view of the holder assembly 30. FIG. 3B illustrates how the latex insert 32 is stretched over the adaptor 31 and how a pressure seal is established due to compression of the latex insert 32 between the adaptor 31 and the holder base 46, when the adaptor 31 is fully screwed into the holder base 46. Note an array of different size or diameter, latex insert 32 are used to correctly hold each test sample having different size and shape, without significant compression of the sample and with a minimal amount of air leakage between the sample and the latex insert 32. For all practical purposes, as long as the leakage is held to an insignificant amount or is minimal, the pressure indicated by the pressure transducer 13 is the same as the pressure in the sample holder 30 for all practical purposes. The adaptor 31 has a row of small holes 44 arranged circumferentially so that it is in communion with the outer circumferential zone between the holder base 46 and the adaptor 31. Hence, when a vacuum is applied through the vacuum tube 24 (via the inlet tube 15 by turning on the switch 8 as shown in FIG. 1A), a negative pressure is created in the area between the latex insert 32 and the adaptor 31 causing the latex insert 32 to flatten out against the walls of the adaptor 31, and thus allowing for the insertion or removal of the test sample 41. When no vacuum is applied, the latex insert 32 gently constricts around the test sample 41 as shown in FIG. 3C.

Weighing device

Referring to FIG. 4, FIG. 4 illustrates how an accurate weighing instrument (analytical balance) is utilized in conjunction with the other subsystems of the porosity-meter. Typical analytical balances have, in addition to side doors, a top door to the weighing platform. The weighing balance 42 is positioned generally in the close vicinity of the instrument box 25, or more specifically at the side of the instrument box 35, where the sample holder assembly 30 is attached. Both the weighing balance 42 and the instrument box 35 are placed on a stable platform. A fluid container, typically with a wide opening, is placed on the platform, and the test sample is lowered, through the top opening of the balance, to the fluid container. The fluid container is centered about the balance. The sample is positioned in close vertical proximity of the fluid surface by means of the horizontal and coarse vertical adjustment means previously described. Final adjustments are made, when necessary, by means of the linear slide stage mechanism 19.

Advancing capillary pressure distribution

The advancing capillary pressure distribution of the sample with respect to the particular application wetting fluid is determined as follows. The fluid is placed in a wide diameter shallow dish set on an analytical balance and the balance is tared or zeroed. Note that the evaporation rate of the wetting fluid should be measured prior to the measurement of the advancing capillary pressure distribution. A high enough steady and controlled pressure is applied to the sample holder such that when the sample is lowered so that the bottom end just touches of the applied wetting fluid (in a shallow dish), little or no fluid is absorbed by the sample. In other words, the applied pressure is just greater than the highest capillary pressure of the sample. Sometimes it is necessary to determine this starting pressure point by trial and error—one or more of the sample pieces may thus be used to establish this starting point. Preferably the starting applied pressure is such that there is a very low or gentle amount of agitation due to bubbles that are formed at the bottom of the sample portion immersed in the fluid.

The highly controlled stable pressure is then incrementally lowered in small intervals. As the pressure is reduced additional fluid is absorbed by the sample and the balance indicates a corresponding loss of fluid from the dish. At each pressure, the absorption of fluid into the sample is at first rapid and eventually this rate of change of weight slows down exponentially. This is allowed to continue until a pseudo equilibrium is reached i.e. the rate of change of fluid loss from the dish is minimal, typically slightly higher than the evaporation rate of the fluid. This weight, pressure and time are recorded and the next lower pressure is applied to the sample holder. This process is continued until zero pressure is applied and equilibrium is reached at this zero pressure. This completes the data acquisition part for the advancing capillary distribution determination.

The advancing capillary pressure distribution can be calculated from absorbed weight (or volume) versus applied pressure data as follows. If $f(P_a)$ is the cumulative average cross sectional area based advancing capillary pressure distribution function, then it can readily be shown that any change in the slope of the weight-pressure curve is due to the beginning of filling of new or fresh zones or "pores" that have higher capillary pressure than the current applied pressure. This is mathematically expressed as:

$$(dW/dP_a)_{P_a} = -(A_c E)_e f(P_a)/g \qquad (5)$$

where W is the cumulative weight absorbed by the sample (e.g. the weight of fluid in the sample), after adjusting for evaporation at each pressure interval, i.e. this has the opposite sign as the weight indicated by the balance; $P_a$ is the advancing capillary pressure and it can be readily shown that it is numerically equal to the applied pressure, $P_{app}$ (Note that $dP_a$ is also equal to $dP_{app}$); $A_c$ is the cross sectional area of the sample assuming that the sample has a uniform cross section; E is the fractional porosity defined as the void fraction; $(A_c E)_e$ is the effective cross sectional void area, considering the possibility that there may be void zones within the sample that are not connected to the rest of the porous structure or are otherwise sealed off; and g is the acceleration due to gravity. Note that if the cross-sectional area $(A_c E)_e$ is truly the average representation of the entire length of the uniform cross section area sample, then $f(P_a)$ may also be considered to be the average volume based advancing capillary pressure distribution.

From equation 5, $f(P_a)$ can be determined as follows:

$$f(P_a) = -g(dW/dP_a)P_a/(A_cE)_e \qquad (2)$$

The capillary distribution function, $f(P_a)$ may be interpreted as the cumulative average fractional void space or fractional cross sectional area of the sample that has a capillary pressure greater than $P_a$. For example, a value of $f(P_a)=0.5$, means that 50% of the average cross sectional area or volume of the reservoir has a capillary pressure greater than $P_a$.

Figure 6:
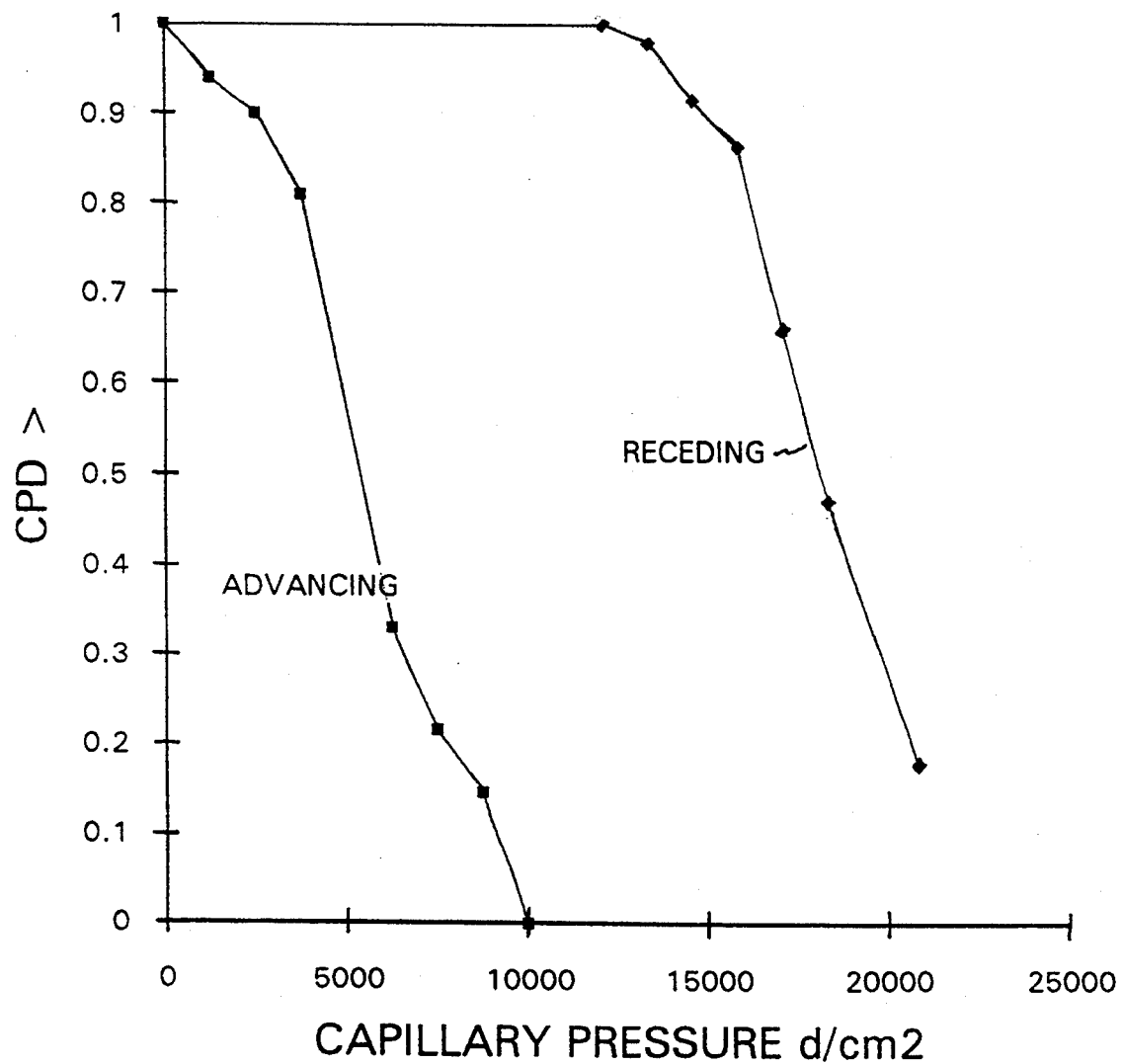
FIG. 6 is a graph illustrating the calculated advancing and receding capillary distribution curves of a typical fibrous marker pen reservoir.

The primary assumptions in developing equation 1 are: a) the distribution function is continuous; and b) there are a large enough number of zones or "pores" such that the distribution is uniform across the vertical length of the sample. This means that although each zone or "pore" is allowed to change its shape or form (morphology), these changes do not significantly affect the capillary pressure distribution (as a whole) significantly, at any cross section. In fact, if any of these conditions are not met, then the calculations show slight reversals in the cumulative distribution function, i.e., instead of $f(P_a)$, continuously decreasing as $P_a$ increases, there are small increases instead. This is illustrated in FIG. 6, which shows typical advancing and receding capillary pressure distributions for a fibrous ink marker reservoir. Thus, additional detail regarding the structure (i.e., deviation from above conditions) is further revealed. In FIG. 6, CPD refers to the cumulative fractional capillary pressure distribution.

Using the boundary condition, $$f(0) - 1 \text{ i.e. when } P_a = 0 \qquad (6)$$

in equation 2, it can be shown that the effective void area is estimated by:

$$(A_cE)_e = -g(dW/dP_a)P_a=0 \qquad (7)$$

Note that it is often desirable instead to base the capillary pressure distribution calculation on the overall or calculated void cross section area, (AcE). In this case (AcE) is used instead of $(A_cE)_e$ in equation 2.

If the sample height is lower than the maximum capillary pressure, then this method is applicable only for a range of applied pressure, such that the fluid first reaches the top of the porous sample. In other words, in this case, the advancing capillary pressure distribution can be investigated for a limited range of capillary pressure. This is because these short capillary zones having higher capillary pressure than the applied pressure, cannot continue to absorb fluid since their height is too small. Under these conditions, the equation 2, above is no longer valid, and hence the analysis can only proceed until this occurs.

Assuming cylindrical "pores", as in mercury porosimetry, the "pore" size distribution can be determined based on the advancing capillary distribution calculations, provided the contact angle (between the solid sample and the wetting fluid), theta, is known or previously measured by other methods. The relationship between the capillary pressure and pore radius, R is:

$$P_a = 2 S \cos(theta)/R \qquad (8)$$

where S is the surface tension of the fluid in contact with the sample. Hence $P_a$ may be replaced by R, in the final calculations and thereby resulting in an advancing interface based "pore" size distribution. It should be noted that this "pore" size distribution is obtained by simply converting the uniquely defined capillary pressure distribution function, rather than starting with a pore size distribution function to result in equation 1 (cf., Adamson 1976). Hence this pore size distribution function should be, in general, different from that measured by Hg porosimetry.

Referring to FIG. 1A to FIG. 4, the measurement of the advancing capillary pressure distribution is conducted with the apparatus described above as follows. The fluid is placed in a wide mouth shallow petri dish 43 or another similar container and placed on the platform of the weighing balance 42. The sample 41 is wrapped with a film 45, as shown in FIG. 5, if the film is not already part of the porous sample. The 3-way valve 11 is directed to the maximum vacuum position such that the maximum vacuum is directed to the sample holder 30. The switch 8 is turned on so as to create the vacuum, and thereby opening the latex insert 32 within the sample holder 30. The top of the sample is then inserted into the sample holder and the switch 8 is turned off, thereby releasing the vacuum from the sample holder, and enabling the sample holder to grip the porous sample.

The top door of the weighing balance 42 is opened and the sample position is then coarsely adjusted by means of the horizontal adjustment bracket 40 and the coarse vertical adjustment of the pressure tube 23 as described above. The sample is positioned so that it almost touches the fluid surface within the weighing balance. The pressure to the sample 41 is adjusted to the maximum anticipated advancing capillary pressure of the sample. This is done by adjusting the metering valve 3 and the pass valve 5. The weighing balance 42 is tared or zeroed, and a stop watch is started at this point. The sample, under the applied pressure, is then lowered by means of the fine vertical linear slide stage mechanism 19, so that the sample just touches the fluid surface in the shallow petri dish 43. Due to circumferential rise of the fluid along the sample 41, the weight on the balance may be reduced somewhat. If this is not due to absorption into the sample, then this weight may be further tared. Generally speaking this amount of weight reduction is negligible compared to the total weight that the sample will eventually absorb, and hence may be ignored. Often, a trial sample run is used, in order to determine the starting pressure such that there is little agitation due to bubbles (when the sample touches the fluid surface) and such that there is little or no gain of fluid by the sample.

At this point, if the air bubbles rapidly into the fluid, the pressure is quickly reduced via valves 3 and 5, so as to prevent the fluid from splashing on to the outer surface of the sample 41. The pressure is reduced so that the balance display does not fluctuate very rapidly. Generally this occurs at a pressure such that the bubbles are almost eliminated. The balance weight is allowed to come to a pseudo-equilibrium, such that a minimum absolute (non-negative) predefined rate of absorption is achieved. This minimum rate is typically chosen to be slightly higher than the absolute (non-negative) value of the evaporation rate of the fluid that is determined prior to conducting the capillary pressure distribution measurement. When the pseudo-equilibrium is reached, the applied pressure, the time and the "equilibrium" weight absorbed by the sample at this pressure are recorded. This constitutes the first data point.

The pressure applied to the sample 41 is then reduced slightly, typically by about 0.25 to 0.5 inches of water head by adjusting the fine adjust valves 3 and if necessary, the valve 5. Lowering of the applied pressure enables the fluid to be further absorbed into the sample. When a pseudo-equilibrium, as defined above is reached, the cumulative weight, absorbed cumulative time and the applied pressure are recorded. This process is continued until zero pressure is applied to the sample. It should be noted that the sample must be in contact with the fluid at all times. Some additional fine vertical adjustments, by the linear slide stage mechanism 19 may be required periodically, in order to ensure contact between the sample and the fluid. This depends on the diameter of the fluid dish and the total volume of fluid absorbed by the sample.

The sign of the recorded balance weights is reversed in order to determine the cumulative weight absorbed by the sample since the weight loss by the balance is equal to the weight gain by the sample minus the evaporation rate. Accordingly, the weights (at each pressure) absorbed by the sample are adjusted for evaporation, based upon the previously determined evaporation rate and the cumulative time at that point. The values of the differential term in equation 2 are determined numerically; and the advancing capillary pressure distribution of the porous sample is calculated. FIG. 6 illustrates a typical advancing capillary pressure distribution measured for a marker pen fibrous reservoir using a dye based ink. Note that the y axis label, CPD is the cumulative average cross sectional area based advancing capillary pressure distribution function.

Receding capillary pressure distribution

There is a hysteresis between the fluid absorption (advancing) and release (receding) from the porous structure. The hysteresis exists because the "pores" or zones within the sample are not uniform and consist of expansions and constrictions and dead ends. During the advancing cycle, the constrictions enhance the absorption of the fluid into the porous structure since they have higher capillary pressure. During the receding cycle, the same constrictions retard the release of the fluid from the porous structure since a small constriction will control the release of a generally larger (on an average) "pore". These factors make the receding capillary pressure higher than the advancing capillary pressure for wetting fluids.

For the release or the receding cycle, the reservoir is approximately and uniformly filled completely at the start. This may be done by injection or as follows. The sample is inserted in the sample holder and then lowered until it touches the fluid surface (in the container which is placed on the balance) so that it can absorb some amount of the fluid by capillary action. The weight of fluid in the sample, such that the voids in the sample are approximately filled, is calculated apriori. This weight is equal to the product of the predetermined porosity, overall sample volume and fluid density. Controlled low vacuum is then applied to the sample holder, so as to fill the fluid in the sample to this predetermined saturation level, by observing the balance display and at the same time controlling the amount of vacuum. In practice, it has been determined that if the sample is filled to at least approximately 80% of its void volume, the error in the resulting receding capillary pressure distribution calculation is typically insignificant.

After filling, the sample is still held in the sample holder and is in contact with the surface of the fluid in the dish placed on the balance. No pressure is applied to the sample. When the balance weight is steady, indicating no significant absorption or desorption of fluid from the sample, the balance weight is noted (this is equal in magnitude to Wmax, the initial weight of the fluid in the sample). The applied pressure is then increased in small increments, and the equilibrated weight is recorded for each increment of the applied pressure, as in the advancing case. This is continued until the first bubble appears, and the last data set (i.e., when the bubble appears) is discarded, since this represents conditions not accounted for in the analysis presented below.

Each zone or "pore" has a receding capillary pressure that is higher than the advancing capillary pressure due to the reasons discussed previously. As the pressure is incrementally increased, each zone or "pore", with receding capillary pressure less than the sum of the applied pressure plus the gravitational pressure of the initial column of fluid, will start to release fluid to the container on the balance. As the pressure is increased further additional zones or "pores", with receding capillary pressure less than the new and higher applied pressure plus the gravitational pressure of the INITIAL column of fluid, will also start to release fluid. Mathematically, this is represented as follows:

$$(dW/dP_r)_{Papp} = -f/(P_r)(A_c E)_e/g \tag{9}$$

Note that, as in the advancing case, W is the weight of the fluid in the sample. Further note that f/ is the cumulative average cross sectional area fraction with receding pressure LESS THAN $P_r$, which is the sum of the applied pressure and the gravitational pressure of the initial column of fluid. Hence, $$f/ = (1-f) \tag{10}$$

where f is the greater than based cumulative receding capillary distribution function. Hence, from equations 9 and 10, the receding distribution function $f(P_r)$ is given by:

$$f(P_r) = 1 + [g(dW/dP_r)_{Papp}/(A_c E)_e] \tag{3}$$

As stated above, $P_r$, the receding capillary pressure depends on $P_{app}$ and is given by:

$$P_r = P_{app} + W_{max} g/(A_c E)_e \tag{4}$$

The second term in equation (3), is the gravitational pressure due to the initial column of fluid. A typical receding capillary pressure distribution for a fibrous pen marker reservoir is shown in FIG. 6. If the cross sectional area $(A_c E)_e$ is representative of the entire length of the uniform cross section sample, then $f(P_r)$ may be also considered to be the average volume based receding capillary pressure distribution.

As in the advancing case, it is possible that the effective void area is less than $A_r$ since there may be traps and dead ends from which it is not possible to have any release. This can be calculated by means of the following analysis.

When the absolute value of $dW/dP_r$ is maximum, all areas that are not dead ends should be releasing for a uni-modal porous sample. Any additional application of pressure should not increase the absolute value of $dW/dP_r$. At this point $f=0$ or $f/=1$. Hence from equation (3):

$$(A_r E)_e = (g) \, abs(dW/dP_r)_{max} \quad (11).$$

Here "abs" denotes the absolute value of the derivative. Due to local fluctuations of data, it is important to note that the maximum value of the absolute of the derivative term in equation 11, must be determined using a smooth best fit curve. This evaluation of the effective area is not possible, if the air bubbles exit through the sample prior to achieving the maximum value of abs $(dW/dP_r)$. Since, there is usually this uncertainty, the calculated void area $(A_c E)$ is simply used instead. Sometimes, it is desirable to base the capillary distribution calculation, on this apparent or calculated void cross section, $(A_c E)$. In these cases $(A_c E)$ is used instead of $(A_c E)_e$ in equation (3).

For most samples with high porosity, it is not necessary to estimate the effective void area; however a method for estimation is provided for both the advancing and receding cases. In both cases, it is necessary to know the porosity, E. This porosity E may be calculated by the following equation:

$$E = 1 - W_s/(V \, rho_s), \quad (12)$$

where $W_s$ is the weight of the sample minus the weight of the film wrap, V is the sample volume and $rho_s$ is the density of the solid material that makes up the porous sample.

As in the case of the advancing measurement, the receding capillary pressure distribution can be converted to an equivalent "pore" size distribution by means of equation 8, with the substitution of $P_r$ for $P_a$.

Referring to FIG. 1A to FIG. 4, the receding capillary pressure distribution may be measured using a fresh sample or a sample whose advancing capillary pressure distribution has already been measured, as described above. If the sample has already been used for measurement of the advancing capillary pressure distribution, then its position in the fluid interface, is maintained. If a fresh sample is to be used for receding capillary pressure determination, then the sample 41 is attached to the sample holder 30 and positioned over the fluid surface as described above, but without the application of any air pressure to the sample. In the case of the fresh sample, the balance is tared, the stop watch is started and then the sample is lowered so that it just touches the fluid surface. In this case the sample readily and rapidly absorbs a given amount of fluid. The rate of absorption reduces rapidly until a pseudo-equilibrium is reached.

In both cases, the sample is filled to preferably 100%, but at least about 80% of the void volume of the sample. This amount is predetermined based on the overall volume, sample porosity of the sample and the density of the fluid. Additional filling is accomplished by first switching the 3-way valve 11 to the controlled low vacuum setting. Vacuum is applied carefully to the sample holder by slowly opening the vacuum metering valve 12. Application of vacuum enables further absorption of the fluid into the reservoir in case the average advancing capillary pressure is not high enough to fill the voids in the sample. This step is necessary in order to meet the necessary conditions stated previously in the summary of the receding capillary pressure distribution method.

The total weight loss from the balance and the elapsed time is then noted. The balance should, at that point, indicate the amount of the fluid in the reservoir minus the evaporation loss, provided the sign on the balance is reversed. The weight absorbed, $W_{max}$ is then calculated by adjusting for the evaporation loss. The pressure to the sample is then increased by a small amount, typically by 0.25 to 0.5 inches of water column, by adjusting the fine adjust valve 3 and the air suction valve 5. This typically causes a small amount of the fluid or no fluid to release from the test sample, thereby increasing the weight of the balance, i.e., the balance now reflects a lower or approximately the same negative weight, after taking into account evaporation loss. The balance weight is allowed to reach to a pseudo-equilibrium, as defined for the advancing case, and the pressure, elapsed time and weight are recorded. The pressure is then increased incrementally again, and the entire process is repeated until eventually the air bubbles penetrate through the test sample 41 and appear in the fluid dish 43. The last data set, corresponding to the appearance of bubbles, is discarded.

As in the advancing case, the weights are adjusted for evaporation, and the sign on the balance weights are reversed in order to get the values of the fluid in the sample. The differential terms in equations 3 are numerically calculated; and the receding capillary pressure distribution is calculated according to the method presented in the summary of the invention.

While the invention has been particularly shown and described with reference to the preferred embodiments, it will be apparent to those who are skilled in the art that changes in form and detail may be made without departing from the spirit and scope of the invention as set forth in the appended claims.

What is claimed is:

1. A method for measuring the advancing capillary pressure distribution of a porous sample, comprising the steps of:

applying a pressure to the porous sample and placing the porous sample in contact with a wetting fluid, said applied pressure being high enough to prevent or to enable only limited absorption of the wetting fluid into the porous sample;

incrementally reducing the applied pressure in intervals and determining the weight absorbed by the porous sample from the wetting fluid at each interval of the reduced pressure; and determining the advancing capillary pressure distribution based upon the applied pressure at each interval and the cumulative weight absorbed by the porous sample at each applied pressure.

2. The method as claimed in claim 1, further comprising the steps of:

measuring a contact angle between the porous sample and the wetting fluid, and the surface tension of the wetting fluid; and calculating the pore size distribution based upon the advancing capillary pressure distribution, the contact angle, and the surface tension of the wetting fluid.

3. The method as claimed in claim 1, wherein the advancing capillary pressure distribution is calculated based upon the following equation:

$$f(P_a) = -g(dW/dP_a)P_a/(A_c E)_e$$

where $f(P_a)$ is the average sample cross section area dependent advancing capillary pressure cumulative distribution function, W is the weight of wetting fluid absorbed by the porous sample at each interval of the reduced pressure, $P_a$ is the advancing capillary pressure, and is equal to the applied pressure, $(A_c E)_e$ is the effective cross sectional void area of the porous sample, and g is acceleration due to gravity.

4. The method as claimed in claim 3, wherein $(A_c E)_e$ is the product of cross-sectional area of the porous sample $A_c$ times its fractional porosity or void fraction E.

5. The method as claimed in claim 3, wherein $(A_c E)_e$ is equal to $-g(dW/dP_a)_{P_a=0}$, where the derivative of W with respect to the advancing capillary pressure is evaluated at $P_a=0$.

6. The method as claimed in claim 3, further comprising:
 determining the pore size distribution based upon the advancing capillary pressure distribution, wherein measurements are made for the contact angle, and the surface tension of the wetting fluid; and
 determining the corresponding cylindrical pore size R of the porous sample based upon the following equation:

$$R = 2\,S\,\cos(\theta)/P_a,$$

where S is the surface tension of the wetting fluid in contact with the porous sample, $\theta$ is an angle of the porous sample in contact with the wetting fluid, and $P_a$ is the advancing capillary pressure.

7. A method for measuring receding capillary pressure distribution of a porous sample, comprising the steps of:
 performing a selected one of:
  a first series of steps comprising of: a) placing the porous sample in contact with a wetting fluid, b) allowing the porous sample to absorb the wetting fluid without application of any pressure on the porous sample, and c) if necessary, applying vacuum to the porous sample so as to enable the voids of the porous sample to be at least eighty percent filled with the wetting fluid; or
  a second series of alternate steps comprising of: a) injecting the porous sample with the wetting fluid so as to fill at least eighty percent of the voids of the porous sample, and b) placing the porous sample in contact with the wetting fluid; and then:
 applying a pressure to the porous sample and incrementally increasing the applied pressure in intervals to make a determination of the wetting fluid remaining in the porous sample at each interval with a corresponding increased pressure; and
 calculating the receding capillary pressure distribution based upon the increased pressure at each interval, the initial or maximum weight of the wetting fluid held in the porous sample and the wetting fluid remaining in the porous sample at each interval.

8. The method as claimed in claim 7, further comprising the steps of:
 measuring a contact angle between the porous sample and the wetting fluid, and the surface tension of the wetting fluid; and
 calculating the pore size distribution based upon the receding capillary pressure distribution, the contact angle, and the surface tension of the wetting fluid.

9. The method as claimed in claim 7, wherein the receding capillary pressure distribution is calculated based upon the following equation:

$$f(P_r) = 1 + [g(dW/dP_r)P_{app}/(A_c E)_e]$$

where $f(P_r)$ is the average cross section area based receding cumulative capillary pressure distribution function, W is the cumulative weight of the wetting fluid remaining in the porous sample at each interval of the increased pressure, $(A_c E)_e$ is the effective cross sectional void area of the porous sample, g is acceleration due to gravity, $P_r$ is the receding capillary pressure which is equal to the sum of the applied pressure plus the initial gravitational pressure due to the fluid and is given by the equation $P_r = P_{app} + W_{max} g/(A_c E)_e$ where $P_{app}$ is the applied pressure and $W_{max}$ is the initial or the maximum weight of the wetting fluid filled into the porous sample.

10. The method as claimed in claim 9, further comprising the step of calculating the pore size R of the porous sample based upon the following equation:

$$R = 2\,S\,\cos(\theta)/P_r,$$

where S is the surface tension of the wetting fluid, $\theta$ is the contact angle of the porous sample in contact with the wetting fluid, and $P_r$ is the receding capillary pressure.

11. The method as claimed in claim 9, wherein said $(A_c E)_e$ is equal to g times the maximum of the absolute value of $(dW/dP_r)$.

12. A method for measuring the advancing and receding capillary pressure distribution of a porous sample, comprising the steps of:
 applying air pressure to the porous sample and placing the porous sample in contact with a wetting fluid, said applied air pressure being high enough to prevent or to enable only limited absorption of the wetting fluid into the porous sample;
 incrementally reducing the applied air pressure in intervals to make a first determination of the weight absorbed by the porous sample from the wetting fluid at each interval of the reduced air pressure;
 calculating the advancing capillary pressure distribution based upon the applied air pressure at each interval and the weight absorbed by the porous sample at each interval;
 applying vacuum, only if necessary, to the porous sample so as to fill the porous sample with the wetting fluid, to at least 80% of the void volume of the porous sample;
 applying air pressure to the porous sample and incrementally increasing the applied air pressure in intervals to make a second determination of the wetting fluid released from the porous sample at each interval with a corresponding increased air pressure; and
 calculating the receding capillary pressure distribution based upon the air pressure at each interval, the initial or maximum weight of the wetting fluid held in the sample and the wetting fluid remaining in the porous sample at each interval.

13. The method as claimed in claim 12, further comprising the steps of:

measuring a contact angle between the porous sample and the wetting fluid, and the surface tension of the wetting fluid; and calculating the pore size distribution based upon the advancing capillary pressure distribution, the contact angle, and the surface tension of the wetting fluid.

14. The method as claimed in claim 12, further comprising the steps of:

measuring a contact angle between the porous sample, and the wetting fluid, and the surface tension of the wetting fluid; and calculating the pore size distribution based upon the receding capillary pressure distribution, the contact angle, and the surface tension of the wetting fluid.

15. The method as claimed in claim 12, wherein the advancing capillary pressure distribution is calculated based upon the following equation:

$$f(P_a) = -g(dW/dP_a)P_a/(A_cE)_e,$$

where $f(P_a)$ is the average sample cross section area based advancing capillary pressure cumulative distribution function, W is the cumulative weight of wetted fluid absorbed by the porous sample at each interval of the reduced air pressure, after adjusting for evaporation, $P_a$ is the advancing capillary pressure and is equal to the applied pressure, $P_{app}$, $(A_cE)_e$ is the effective cross sectional void area of the porous sample, and g is the acceleration due to gravity.

16. The method as claimed in claim 15, further comprising the step of calculating the corresponding cylindrical pore size R of the porous sample based upon the following equation:

$$R = 2 S \cos(\theta)/P_a,$$

where S is the surface tension of the wetting fluid in contact with the porous sample, $\theta$ is an angle of the porous sample in contact with the wetting fluid, and $P_a$ is the advancing capillary pressure.

17. The method as claimed in claim 12, wherein the receding capillary pressure distribution is calculated based upon the following equation:

$$f(P_r) = 1 + [g(i\ dW/dP_r)P_{app}/(A_cE)_e],$$

where $f(P_r)$ is the average cross section area based receding cumulative capillary pressure distribution function, W is the weight of the fluid remaining in the porous sample at each interval of the increased air pressure, $(A_cE)_e$ is the effective cross sectional void area of the porous sample, g is acceleration due to gravity, $P_r$ is the receding capillary pressure which is equal to the sum of the applied pressure plus the initial gravitational pressure due to the fluid and is given by the equation $P_r = P_{app} + W_{max}g/(A_rE)_e$, where $P_{app}$ is the applied air pressure and $W_{max}$ is the initial weight of the wetting fluid filled into the porous sample.

18. The method as claimed in claim 17, further comprising the step of calculating the pore size R of the porous sample based upon the following equation:

$$R = 2 S \cos(\theta)/P_r,$$

where S is the surface tension of the wetting fluid, $\theta$ is the contact angle of the porous sample in contact with the wetting fluid, and $P_r$ is the receding capillary pressure.

19. A capillary pressure measuring device for determining the advancing and receding capillary pressure distributions of a porous sample using a wetting fluid, comprising:

a sample holder having a pressure inlet and a vacuum inlet, for holding the porous sample within a housing;

a vertical positioning mechanism for adjusting the porous sample in a vertical direction to place the porous sample in contact with the wetting fluid within said housing;

a pressure control system having a vacuum producing subsystem, for applying air pressure to the porous sample via said pressure inlet of said sample holder, and producing a vacuum within said housing via said vacuum inlet of said sample holder, said pressure control system applying the air pressure to the porous sample and incrementally reducing the applied air pressure in intervals for making a measurement of the advancing capillary pressure distribution based upon the reduced air pressure at each interval and the weight absorbed by the porous sample from the wetting fluid at each interval of the reduced air pressure, said pressure control system further applying the air pressure to the sample and incrementally increasing the applied air pressure in intervals for making a measurement of the receding capillary distribution based upon the increased air pressure at each interval and the wetting fluid released from the porous sample at each interval; and a weighing device for weighing the wetting liquid to determine the weight absorbed by the porous sample from the wetting fluid at each interval of the reduced air pressure, and the wetting fluid released from the porous sample at each interval of the increased air pressure.

20. The capillary pressure measuring device as claimed in claim 19, further comprising:

means for measuring a contact angle between the porous sample and the wetting fluid, and the surface tension of the wetting fluid; and means for calculating the pore size distribution based upon the advancing and receding capillary pressure distribution, the contact angle, and the surface tension of the wetting fluid.

21. The capillary pressure measuring device as claimed in claim 19, wherein the advancing capillary pressure distribution is calculated based upon the following equation:

$$f(P_a) = -g(dW/dP_a)P_a/(A_cE)_e,$$

where $f(P_a)$ is the average sample cross section area based advancing capillary pressure cumulative distribution function, W is the cumulative weight of wetting fluid absorbed by the porous sample at each interval of the reduced air pressure, after adjusting for evaporation, $P_a$ is the advancing capillary pressure and is equal to the applied pressure, $(A_cE)_e$ is the effective s cross sectional void area of the porous sample, and g is gravity.

22. The capillary pressure measuring device as claimed in claim 21, wherein said pore size calculating means calculates the pore size R of the porous sample based upon the following equation:

$$R = 2\,S\,\cos(\theta)/P,$$

where S is the surface tension of the wetting fluid in contact with the porous sample, $\theta$ is an angle of the porous sample in contact with the wetting fluid, and P is one of the advancing and receding capillary pressure.

23. The capillary pressure measuring device as claimed in claim 19, wherein the receding capillary pressure distribution is calculated based upon the following equation:

$$f(P_r) = 1 + [g(dW/dP_r)P_{app}/(A_c E)_e],$$

where $f(P_r)$ is the average cross section area based receding cumulative capillary pressure distribution function, W is the weight of the wetting fluid in the porous sample at each interval of the increased air pressure, $(A_c E)_e$ is the effective cross sectional void area of the porous sample, g is acceleration due to gravity, $P_r$ is the receding capillary pressure which is equal to the sum of the increased pressure plus the initial gravitational pressure due to the wetting fluid and is given by the equation of $P_r = P_{app} + W_{max} g/(ArE)_e$, where $P_{app}$ is the applied pressure and $W_{max}$ is the initial weight of the wetting fluid filled into the porous sample.

24. The capillary pressure measuring device as claimed in claim 19, wherein said pressure control system having a vacuum producing subsystem comprises:
   air supply source for supplying the applied air pressure;
   a pressure tube connected to the pressure inlet of said sample holder;
   a vacuum tube connected to the vacuum inlet of said sample holder;
   pressure regulator means connected to said air supply source, for primary regulation of the applied air pressure;
   a bypass air flow, with a regulating value for additional regulation of the applied air pressure;
   a air accumulator for damping of any pressure fluctuations;
   a venturi disposed between said vacuum tube and said air supply source;
   a first solenoid valve connected between said venturi and said air supply source, for enabling the applied air pressure to flow through said venturi to produce said vacuum at said vacuum tube;
   second solenoid valve connected between said pressure tube and said air accumulator, for enabling the constant air pressure to flow through said pressure tube and preventing the vacuum from leaking into said air accumulator;
   a switch electrically connected with said first and second solenoid valves, for alternatively controlling operation of one of said first and second solenoid valves; and a pressure transducer for measuring the air pressure in said pressure tube.

25. The method as claimed in claim 1, wherein the porous sample is enclosed in a film and sealed along a longitudinal axis so that only the top and bottom ends of the porous sample are open to the air pressure.

26. The method as claimed in claim 7, wherein the porous sample is enclosed in a film and sealed along a longitudinal axis so that only the top and bottom ends of the porous sample are open to the air pressure or applied vacuum.

27. The method as claimed in claim 12, wherein the porous sample is enclosed in a film and scaled along a longitudinal axis so that only ,the top and bottom ends of the porous sample are open to the air pressure or applied vacuum.

28. The capillary pressure measuring device as claimed in claim 19, wherein the porous sample is enclosed in a film and sealed along a longitudinal axis so that only the top and bottom ends of the porous sample are open to the air pressure.

29. The capillary pressure measuring device as claimed in claim 19, wherein said pressure control system having a vacuum producing subsystem comprises:
   air supply source for supplying the applied air pressure;
   pressure regulator means connected to said air supply source, for primary regulation of the applied air pressure;
   a first flow branch including a vacuum tube for applying vacuum to the vacuum inlet of said sample holder;
   a second alternate flow branch including a pressure tube for applying pressure to the pressure inlet of said sample holder;
   a first solenoid valve disposed between the vacuum tube and said air supply source and placed in the first flow branch;
   a venturi connected between the first solenoid valve and the vacuum tube which is connected to the throat of the venturi, the main air flow of the venturi being discharged to the atmosphere;
   a flow accumulator disposed between the second alternate flow branch and the pressure tube, for damping of any pressure fluctuations;
   a second solenoid valve disposed between the flow accumulator and the air supply source and placed in the second alternate flow branch;
   a third flow branch including a fine pressure regulator, for providing a bypass flow branch resulting in a fraction of the flow bypassing the flow accumulator, and thus providing for additional regulation of the applied air pressure;
   an exit to the third flow branch that allows for the discharge of bypass air to the atmosphere;
   a switch electrically connected with the first and second solenoid valves, so as to allow flow through either the first flow branch or the second alternate flow branch; and
   a pressure transducer connected to the sample holder for the measurement of both pressure and vacuum applied to the porous sample.

30. The method as claimed in claim 2, wherein said contact angle between the porous sample and the wetting fluid is measured using a substitute sample in a non-porous form having same wettability as the porous sample.

31. The method as claimed in claim 8, wherein said contact angle between the porous sample and the wetting fluid is measured using a substitute sample in a non-porous form having same wettability as the porous sample.

32. The method as claimed in claim 12, wherein said contact angle between the porous sample and the wetting fluid is measured using a substitute sample in a non-porous form having same wettability as the porous sample.

33. The method as claimed in claim 14, wherein said contact angle between the porous sample and the wetting fluid is measured using a substitute sample in a non-porous form having same wettability as the porous sample.

34. The capillary pressure measuring device as claimed in claim 20, wherein said means for measuring the contact angle between the porous sample and the wetting fluid measures said contact angle using a substitute sample in a non-porous form having same wettability as the porous sample.

* * * * *